(12) United States Patent
Ujita

(10) Patent No.: US 8,816,123 B2
(45) Date of Patent: Aug. 26, 2014

(54) METHOD FOR PRODUCING ALKYL 5-METHYL-5-HEXENOATE

(75) Inventor: Katsuji Ujita, Niigata (JP)

(73) Assignee: Kuraray Co., Ltd., Okayama (JP)

( * ) Notice: Subject to any disclaimer, the term of this patent is extended or adjusted under 35 U.S.C. 154(b) by 38 days.

(21) Appl. No.: 13/515,737

(22) PCT Filed: Dec. 1, 2010

(86) PCT No.: PCT/JP2010/071479
§ 371 (c)(1),
(2), (4) Date: Jun. 13, 2012

(87) PCT Pub. No.: WO2011/074416
PCT Pub. Date: Jun. 23, 2011

(65) Prior Publication Data
US 2012/0253062 A1    Oct. 4, 2012

(30) Foreign Application Priority Data
Dec. 15, 2009  (JP) ................. 2009-284477

(51) Int. Cl.
*C07C 69/533*    (2006.01)
*C07C 67/32*    (2006.01)

(52) U.S. Cl.
CPC ................................. *C07C 67/32* (2013.01)
USPC ..................................................... 560/205

(58) Field of Classification Search
CPC ..................................................... C07C 67/32
See application file for complete search history.

(56) References Cited

U.S. PATENT DOCUMENTS

| | | |
|---|---|---|
| 4,769,492 A | 9/1988 | Kaieda et al. |
| 5,955,627 A | 9/1999 | Nakazawa et al. |
| 6,500,990 B2 * | 12/2002 | Asada et al. ........... 568/341 |

FOREIGN PATENT DOCUMENTS

| | | |
|---|---|---|
| JP | 62 45 | 1/1987 |
| JP | 8 245508 | 9/1996 |
| JP | 9 216849 | 8/1997 |
| JP | 10 316621 | 12/1998 |

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Fraenkel et al, Journal of the American Chemical Society, Decarboxylation of Malonic Acid in Quinoline and Related Media, 1954, 76, pp. 15-18.*
Tanabe, K., et al., "Studies on Ring-Closing Metathesis for the Formation of the 11-Membered Ring System of Daphnezomine C," Bulletin of the Chemical Society of Japan, vol. 80, No. 8, pp. 1597-1604, (2007).
Beckwith, A.L.J., et al., "Aluminium-Chloride-Promoted Reactions of Ethyl Acrylate with Olefins," Australian Journal of Chemistry, vol. 30, pp. 2733-2739, (1977).
International Search Report Issued Feb. 8, 2011 in PCT/JP10/71479 Filed Dec. 1, 2010.
Extended European Search report issued on May 22, 2013 in Application No. 10837445.5.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

A decarboxylation reaction of a (3-methyl-3-butenyl)malonic acid dialkyl ester, carried out by heating in the presence of water and a base, produces an alkyl 5-methyl-5-hexenoate. The decarboxylation reaction produces the alkyl 5-methyl-5-hexenoate inexpensively and effectively. The base can optionally be a tertiary amine compound or a heterocyclic amine compound. Producing the alkyl 5-methyl-5-hexenoate can optionally further include removing an alcohol.

15 Claims, No Drawings

METHOD FOR PRODUCING ALKYL 5-METHYL-5-HEXENOATE

This application is a National Stage of PCT/JP10/071479 filed Dec. 1, 2010 and claims the benefit of JP 2009-284477 filed Dec. 15, 2009.

TECHNICAL FIELD

The present invention relates to a method for producing an alkyl 5-methyl-5-hexenoate, which is a useful compound as a raw material for an intermediate for pharmaceuticals, agrochemicals and other fine chemical products.

BACKGROUND ART

Known conventional methods for producing an alkyl 5-methyl-5-hexenoate (5-methyl-5-hexenoic acid alkyl ester) include a method of using an ene reaction of an acrylic acid ester and isobutene (see Non-Patent Reference 1) and a method in which a decarboxylation reaction of dimethyl(3-methyl-3-butenyl)malonate is carried out using 2-fold mol of water and equivalent mol of sodium chloride as a nucleophile in N,N-dimethylformamide (DMF) as a solvent (Krapcho reaction) (see Non-Patent Reference 2).

CITATION LIST

Non-Patent References

Non-Patent Reference 1: Australian Journal of Chemistry, 1977, Vol. 30, p. 2733
Non-Patent Reference 2: Bull. Chem. Soc. Jpn., 2007, Vol. 80, No. 8, p. 1597

SUMMARY OF THE INVENTION

Problems to be Solved by the Invention

The method described in the Non-Patent Reference 1 has drawbacks in that the yield of the final product to be obtained is low and an isomer which is difficult to be isolated is produced as a by-product in approximately 70%.

In the method described in the Non-Patent Reference 2, sodium chloride is needed to be used as a nucleophile. In addition, it has a drawback in that chloromethane ($CH_3Cl$), a toxic compound, is produced as a by-product.

Thus, an object of the present invention is to provide a method capable of industrially inexpensively and efficiently producing an alkyl 5-methyl-5-hexenoate.

Means for Solving the Problems

That is, the present invention is a method for producing an alkyl 5-methyl-5-hexenoate represented by the following Chemical formula (2):

[Chemical formula 2]

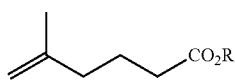

(2)

(wherein R represents a linear or branched alkyl group having 1 to 12 carbon atoms) (hereinafter may be referred to as Compound (2)), comprising a decarboxylation reaction of a (3-methyl-3-butenyl)malonic acid dialkyl ester represented by the following Chemical formula (1):

[Chemical formula 1]

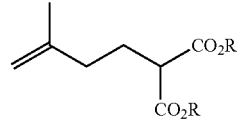

(1)

(wherein R is as defined above)
(hereinafter may be referred to as Compound (1)) carried out by heating in the presence of water and a base.

Effects of the Invention

According to the present invention, an alkyl 5-methyl-5-hexenoate, which is a useful compound as a raw material for an intermediate for pharmaceuticals, agrochemicals and other fine chemical products, can be produced industrially inexpensively and efficiently.

MODES FOR CARRYING OUT THE INVENTION

Specific embodiments for carrying out the present invention will now be described in more detail.

In the production method of the present invention, Compound (1) is used as a starting material.

In the formula, R represents a linear or branched alkyl group having 1 to 12 carbon atoms. The number of carbons in R is preferably 1 to 8, more preferably 1 to 4, and further preferably 1 or 2. Examples of R include methyl group, ethyl group, n-propyl group, isopropyl group, n-butyl group, isobutyl group, sec-butyl group, tert-butyl group, hexyl group, octyl group, decyl group, dodecyl group and the like. Among these, methyl group and ethyl group are especially preferred.

A commercially available product of Compound (1) can be used, if any. In addition, Compound (1) can be prepared by synthesis. The method for synthesizing Compound (1) is not particularly limited, and known knowledge in the art of organic chemistry can be appropriately referred to.

An example of the method for synthesizing Compound (1) includes a method described below in Production Examples 1 and 2. In such a method, first, isoprenol is reacted with methanesulfonyl chloride in the presence of a base such as triethylamine to obtain methanesulfonic acid isoprenyl ester. Next, if needed, the obtained product is isolated and purified by a conventional method, and the obtained methanesulfonic acid isoprenyl ester is reacted with a malonic acid dialkyl ester in the presence of a base such as sodium ethoxide. As needed, a neutralization step is carried out using an acid to obtain Compound (1).

In addition, Compound (1) may be synthesized by applying e.g. the method described in Journal of Organic Chemistry, 61, 2266 (1996).

In the production method of the present invention, a decarboxylation reaction of Compound (1) as the starting material is carried out by heating to obtain Compound (2) as the objective product.

The heating conditions are not particularly limited, and it is necessary to proceed the decarboxylation reaction. The heating temperature is preferably 100 to 200° C., more preferably 130 to 200° C., and further preferably 150 to 180° C. The reaction time is preferably for 10 minutes to 30 hours, and more preferably for 1 to 15 hours. The pressure condition of the reaction system is not particularly limited. The reaction can be carried out under normal, increased or reduced pressure, and the normal pressure is usually preferred.

The amount of water to be used in the production method of the present invention is not particularly limited, and is preferably 1 to 10 mol, and more preferably 1 to 3 mol per 1 mol of Compound (1). Depending on the heating temperature (specifically, when the heating temperature is equal to or higher than the boiling point of water under a pressure condition of the reaction system), water is not added to the reaction system at the beginning, but it is preferred that water be continuously or intermittently added to the reaction system.

The base used in the production method of the present invention includes an amine compound, an alkali metal compound, an alkaline earth metal compound and the like. The base can be used individually or two or more compounds can be used in combination.

Preferred the amine compound includes a tertiary amine compound and a heterocyclic amine compound. Examples of the tertiary amine compound include an aliphatic tertiary amine such as trialkylamine e.g. triethylamine, tripropylamine, tributylamine, trihexylamine and trioctylamine, and a dialkylalkylamine e.g. diethylmethylamine and dibutylethylamine; an alicyclic tertiary amine such as tricycloalkylamine e.g. tricyclohexylamine, dicycloalkylalkylamine e.g. dicyclohexylmethylamine, and cycloalkyldialkylamine e.g. cyclohexyldimethylamine; and an aromatic tertiary amine such as triarylamine e.g. triphenylamine, and aryldialkylamine e.g. N,N-dimethylaniline. Examples of the heterocyclic amine compound include pyridine, methylpyridine, ethylpyridine, quinoline, isoquinoline, quinoxaline, quinazoline, phthalazine, 1-methylimidazole, N,N-dimethylaminopyridine and the like.

Examples of the alkali metal compound include an alkali metal hydroxide such as lithium hydroxide, sodium hydroxide, potassium hydroxide, rubidium hydroxide and cesium hydroxide; an alkali metal carbonate such as lithium carbonate, sodium carbonate, potassium carbonate, rubidium carbonate and cesium carbonate; an alkali metal hydrogen carbonate such as lithium hydrogen carbonate, sodium hydrogen carbonate, potassium hydrogen carbonate, rubidium hydrogen carbonate and cesium hydrogen carbonate; an alkali metal bicarbonate such as lithium bicarbonate, sodium bicarbonate, potassium bicarbonate, rubidium bicarbonate and cesium bicarbonate; an alkali metal alkoxide such as potassium butoxide, potassium ethoxide, potassium methoxide, sodium butoxide, sodium ethoxide, sodium methoxide, lithium butoxide, lithium ethoxide and lithium methoxide; and the like. Examples of the alkaline earth metal compound include an alkaline earth metal hydroxide such as beryllium hydroxide, magnesium hydroxide, calcium hydroxide, strontium hydroxide and barium hydroxide; an alkaline earth metal carbonate such as beryllium carbonate, magnesium carbonate, calcium carbonate, strontium carbonate and barium carbonate; an alkaline earth metal hydrogen carbonate such as beryllium hydrogen carbonate, magnesium hydrogen carbonate, calcium hydrogen carbonate, strontium hydrogen carbonate, barium hydrogen carbonate and rubidium hydrogen carbonate; an alkaline earth metal bicarbonate such as beryllium bicarbonate, magnesium bicarbonate, calcium bicarbonate, strontium bicarbonate and barium bicarbonate; and the like.

The base can be used individually or two or more bases can be used in combination. The base is preferably the amine compound, more preferably the tertiary amine compound or the heterocyclic amine compound, and especially preferably the tertiary amine compound.

The amount of the base to be used is not particularly limited, and is preferably 0.001 to 10 mol and more preferably 0.01 to 1 mol per 1 mol of Compound (1).

The production method of the present invention can be carried out in the presence or absence of a solvent. Examples of the solvent include a saturated aliphatic hydrocarbon such as hexane, heptane and octane; an aromatic hydrocarbon such as benzene, toluene, xylene, cumene, pseudocumene and ethylbenzene; a glycol dimethyl ether such as ethylene glycol dimethyl ether, diethylene glycol dimethyl ether and triethylene glycol dimethyl ether; an ether such as tetrahydrofuran and dioxane; an ester such as ethyl acetate, octyl acetate and methyl butyrate; a halogenated hydrocarbon such as methylene chloride, chloroform and 1,2-dichloroethane; mixtures of these compounds; and the like. When the solvent is used, the amount thereof to be used is not particularly limited, and is preferably not more than 100 parts by mass, more preferably not more than 50 parts by mass, and further preferably not more than 10 parts by mass per 1 part by mass of Compound (1) from the viewpoints of a reaction rate, economic efficiency and the like.

In the production method of the present invention, an alcohol represented by the following Chemical formula (3):

[Chemical formula 3]

(wherein R is as defined above)
is produced as a by-product by decarboxylation of Compound (1). For example, as in Example 1 described below, when diethyl(3-methyl-3-butenyl)malonate (R=ethyl group) is used as the Compound (1), ethanol is produced as a by-product.

In the production method of the present invention, it is preferred that the reaction is carried out while removing the alcohol produced as a by-product produced as described above to the outside of the reaction system. The means for removing the alcohol produced as a by-product to the outside of the reaction system is not particularly limited, preferably, the alcohol is removed by distillation. Whole amount of the alcohol as a by-product can be removed by distillation from moment to moment of the generation, or a part thereof can be distilled off.

Alkyl 5-methyl-5-hexenoate obtained can be isolated and purified by a known isolation and purification means such as filtration, condensation, distillation, extraction, crystallization, recrystallization and column chromatography, or a combination of the above.

Alkyl 5-methyl-5-hexenoate produced by the production method of the present invention is suitably used as a raw material for an intermediate for pharmaceuticals, agrochemicals and other fine chemical products.

EXAMPLES

The present invention is hereunder described in more detail with Examples and the like, but it should be noted that the present invention is not limited to the following Examples.

Production Example 1

In a 2 L four-necked round bottom flask equipped with a condenser, a thermometer, a dropping funnel and a mechanical stirrer, 172 g (2.00 mol) of isoprenol, 222 g (2.20 mol) of triethylamine and 800 g of toluene were placed. To this solution, while maintaining the internal temperature at 5 to 15° C., 240 g (2.10 mol) of methanesulfonyl chloride was added dropwise over 3 hours. After the completion of the dropwise addition, a reaction was carried out at 20° C. for 1 hour. To the obtained reaction solution, 400 g of water was added, and 703 g of an aqueous layer was then isolated to obtain 1127 g of an organic layer, i.e. a solution of methanesulfonic acid isoprenyl ester in toluene.

Production Example 2

Into a 2 L four-necked round bottom flask equipped with a condenser, a thermometer, a dropping funnel and a mechanical stirrer, 374 g (1.1 mol) of a 20% by mass solution of sodium ethoxide in ethanol was added, and to the obtained solution, 176 g (1.1 mol) of diethyl malonate was added dropwise at an internal temperature of 60° C. over 20 minutes. After the completion of the dropwise addition, the obtained reaction solution was stirred for 20 minutes. To the reaction solution, 563 g of a solution of methanesulfonic acid isoprenyl ester in toluene (1 mol) obtained in the Production Example 1 was added dropwise at 60° C. over 2 hours and 20 minutes. After the completion of the dropwise addition, a reaction was carried out at an internal temperature of 80° C. for 6 hours. The obtained reaction solution was cooled to 20° C., and 503 g of 0.2% by mass of hydrochloric acid was added thereto, followed by isolating 898 g of an aqueous layer to obtain 670 g of an organic layer. The organic layer was concentrated in vacuo (bath temperature: 40° C.) to obtain 247 g of crude diethyl(3-methyl-3-butenyl)malonate (net. 185 g, 81% yield (calculated based on isoprenol) measured by an internal standard method using gas chromatography (GC)). 5.0 g (net. 3.7 g) of the obtained crude diethyl(3-methyl-3-butenyl)malonate was purified by distillation (94° C., 267 Pa) to obtain 3.2 g of diethyl(3-methyl-3-butenyl)malonate (GC purity 98%, distillation yield 86%) having the following properties.
$^1$H-NMR spectrum (400 MHz, CDCl$_3$, TMS, ppm) δ: 4.76-4.69 (2H, m), 4.22-4.17 (2H, q, J=7.2 Hz), 3.36-3.31 (1H, m), 2.05-2.03 (2H, m), 1.72-1.58 (2H, m), 1.33-1.22 (3H, t, J=7.2 Hz)

Example 1

In a 1 L four-necked round bottom flask equipped with a distillation column, a thermometer, a dropping funnel and a stirrer tip, 406 g (net. 295 g, 1.29 mol) of crude diethyl(3-methyl-3-butenyl)malonate produced by the same method as in the Production Example 2 and 22.8 g (0.064 mol) of trioctylamine were placed. This solution was heated to 170° C., and to the solution heated to 170° C., 42.3 g (2.35 mol) of water was added dropwise over 12 hours. While water was added dropwise, ethanol produced by the reaction was distilled off to maintain the reaction temperature at 160 to 170° C. After the completion of the reaction, the obtained reaction solution was cooled to 20° C. to obtain 246 g of a reaction solution (ethyl 5-methyl-5-hexenoate: net. 193 g, 96% yield measured by an internal standard method using GC). 246 g of the reaction solution was purified by distillation (78° C., 1733 Pa) to obtain 170 g of ethyl 5-methyl-5-hexenoate (GC purity 99%, distillation yield 88%) having the following properties. In addition, the content of an isomer (ethyl 5-methyl-4-hexenoate) in the purified product was measured by GC to find that it was under the detectable limit.

$^1$H-NMR spectrum (400 MHz, CDCl$_3$, TMS, ppm) δ: 4.73-4.68 (2H, m), 4.15-4.10 (2H, q, J=7.2 Hz), 2.31-2.27 (2H, m), 2.06-2.02 (2H, m), 1.81-1.75 (2H, m), 1.71 (3H, s), 1.27-1.23 (3H, t, J=7.2 Hz)

Example 2

In a 100 mL four-necked round bottom flask equipped with a distillation column, a thermometer, a dropping funnel and a stirrer tip, 9.01 g (net. 6.85 g, 0.03 mol) of crude diethyl(3-methyl-3-butenyl)malonate obtained by the same method as in the Production Example 2 and 0.212 g (0.6 mmol) of trioctylamine were placed. This solution was heated to 170° C., and to the solution heated to 170° C., 2.16 g (0.12 mol) of water was added dropwise over 7 hours. While water was added dropwise, ethanol produced by the reaction was distilled off to maintain the reaction temperature at 160 to 170° C. After the completion of the reaction, the obtained reaction solution was cooled to 20° C. to obtain 5.63 g of a reaction solution (ethyl 5-methyl-5-hexenoate: net. 4.49 g, 95.8% yield measured by an internal standard method using GC). In addition, the content of an isomer (ethyl 5-methyl-4-hexenoate) in the reaction solution was measured by GC to find that it was under the detectable limit.

Example 3

In the same reaction device as in the Example 2, 34.0 g (net. 24.6 g, 0.108 mol) of crude diethyl(3-methyl-3-butenyl)malonate obtained by the same method as in the Production Example 2 and 19.1 g (0.054 mol) of trioctylamine were placed. This solution was heated to 170° C., and to the solution heated to 170° C., 7.76 g (0.43 mol) of water was added dropwise over 10 hours. While water was added dropwise, ethanol produced by the reaction was distilled off to maintain the reaction temperature at 160 to 170° C. After the completion of the reaction, the obtained reaction solution was cooled to 20° C. to obtain 32.03 g of a reaction solution (ethyl 5-methyl-5-hexenoate: net. 16.13 g, 95.6% yield measured by an internal standard method using GC). In addition, the content of an isomer (ethyl 5-methyl-4-hexenoate) in the reaction solution was measured by GC to find that it was under the detectable limit.

Example 4

The same reaction was performed as in the Example 2 except that 10.6 g (0.03 mol) of trioctylamine was used and 2.16 g (0.12 mol) of water was added dropwise over 9 hours. After the completion of the reaction, the obtained reaction solution was cooled to 20° C. to obtain 16.23 g of a reaction solution (ethyl 5-methyl-5-hexenoate: net. 4.59 g, 97.9% yield measured by an internal standard method using GC). In addition, the content of an isomer (ethyl 5-methyl-4-hexenoate) in the reaction solution was measured by GC to find that it was under the detectable limit.

Example 5

The same reaction was performed as in the Example 2 except that 0.125 g of sodium hydrogen carbonate (1.5 mmol) was used in place of 0.212 g of trioctylamine (0.6 mmol). After the completion of the reaction, the obtained reaction solution was cooled to 20° C. to obtain 5.46 g of a reaction solution (ethyl 5-methyl-5-hexenoate: net. 4.24 g, 90.5% yield measured by an internal standard method using GC). In addition, the content of an isomer (ethyl 5-methyl-4-hex-

Example 6

The same reaction was performed as in the Example 2 except that 0.183 g (1.5 mmol) of N,N-dimethylaminopyridine was used in place of 0.212 g (0.6 mmol) of trioctylamine. After the completion of the reaction, the obtained reaction solution was cooled to 20° C. to obtain 5.53 g of a reaction solution (ethyl 5-methyl-5-hexenoate: net. 4.37 g, 93.2% yield measured by an internal standard method using GC). In addition, the content of an isomer (ethyl 5-methyl-4-hexenoate) in the reaction solution was measured by GC to find that it was under the detectable limit.

Comparative Example 1

In a 100 mL four-necked round bottom flask equipped with a distillation column, a thermometer, a dropping funnel and a stirrer tip, 46 g (net. 33.5 g, 147 mmol) of crude diethyl(3-methyl-3-butenyl)malonate obtained by the same method as in the Production Example 2 was placed. This solution was heated to 170° C., and to the solution heated to 170° C., 5.3 g (294 mmol) of water was added dropwise over 12 hours. While the water was added dropwise, ethanol produced by the reaction was distilled off to maintain the reaction temperature at 160 to 170° C. After the completion of the reaction, the obtained reaction solution was cooled to 20° C. to obtain 38 g of a reaction solution (ethyl 5-methyl-5-hexenoate: net. 4.19 g, 17.9% yield measured by an internal standard method using GC). In addition, the content of an isomer (ethyl 5-methyl-4-hexenoate) in the reaction solution was measured by GC to find 17.9 g (78% yield).

Comparative Example 2

In a 100 mL four-necked round bottom flask equipped with a condenser, a thermometer and a stirrer tip, 9.01 g (net. 6.85 g, 0.03 mol) of crude diethyl(3-methyl-3-butenyl)malonate obtained by the same method as in the Production Example 2, 2.1 g (36 mol) of sodium chloride, 1.11 g (61.2 mmol) of water and 45 g of N,N-dimethylformamide (DMF) were placed. This solution was stirred at 135 to 145° C. for 52 hours. After the completion of the reaction, the obtained reaction solution was cooled to 20° C., and the solution was then poured to 300 g of water. The obtained solution was extracted twice with 30 g of hexane to obtain 88.5 g of a reaction solution (ethyl 5-methyl-5-hexenoate: net. 3.93 g, 83.8% yield measured by an internal standard method using GC). In addition, the content of an isomer (ethyl 5-methyl-4-hexenoate) in the reaction solution was 0.28% (ethyl 5-methyl-5-hexenoate 99.72%) by a GC area ratio relative to the objective product.

The invention claimed is:

1. A method, comprising:
heating, in a decarboxylation reaction, a (3-methyl-3-butenyl)malonic acid dialkyl ester of formula (1):

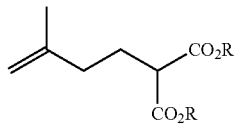
(1)

in the presence of water and a base, to obtain an alkyl 5-methyl-5-hexenoate of formula (2):

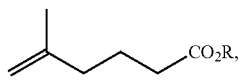
(2)

wherein R is a linear or branched alkyl group having 1 to 12 carbon atoms,
wherein the base is one or more selected from the group consisting of a tertiary amine, a heterocyclic amine, and an alkali metal hydrogen carbonate.

2. The method of claim 1, wherein the base is a tertiary amine compound, a heterocyclic amine compound, or both.

3. The method of claim 1, further comprising:
removing an alcohol of formula (3):

R—OH (3)

to outside of the decarboxylation reaction.

4. The method of claim 2, further comprising:
removing an alcohol of formula (3):

R—OH (3)

to outside of the decarboxylation reaction.

5. The method of claim 1, wherein R is a linear or branched alkyl group having 1 to 8 carbon atoms.

6. The method of claim 5, wherein R is a methyl group or an ethyl group.

7. The method of claim 1, wherein the heating comprises heating the ester of formula (1) to a temperature of from 100 to 200° C.

8. The method of claim 1, wherein the molar ratio of water to the ester of formula (1) in the decarboxylation reaction is from 1:1 to 10:1.

9. The method of claim 1, further comprising continuously or intermittently adding water during the decarboxylation reaction.

10. The method of claim 1, wherein the molar ratio of the base to the ester of formula (1) in the decarboxylation reaction is from 0.001:1 to 10:1.

11. The method of claim 1, wherein the decarboxylation reaction is in the presence of a solvent.

12. The method of claim 1, wherein the base is selected from the group consisting of trioctylamine, sodium hydrogen carbonate, and N,N-dimethylaminopyridine.

13. The method of claim 1, wherein the base is trioctylamine.

14. The method of claim 1, wherein the base is sodium hydrogen carbonate.

15. The method of claim 1, wherein the base is N,N-dimethylaminopyridine.

* * * * *